United States Patent [19]  [11] 4,036,852
Boesten  [45] July 19, 1977

[54] OPTICAL RESOLUTION OF PHENYL-GLYCINE AMIDE

[75] Inventor: Wilhelmus H. J. Boesten, Sittard, Netherlands

[73] Assignee: Stamicarbon B.V., Geleen, Netherlands

[21] Appl. No.: 623,928

[22] Filed: Oct. 20, 1975

[30] Foreign Application Priority Data

Oct. 23, 1974 Netherlands .......................... 7413843

[51] Int. Cl.² ............................................ C07D 207/24
[52] U.S. Cl. ............................. 260/326.45; 260/558 A
[58] Field of Search ........................ 260/326.45, 558 A

[56] References Cited

U.S. PATENT DOCUMENTS 2,528,267  10/1950  Dearborn et al. ............... 260/326.45
2,543,345  2/1951   Waller ............................. 260/326.45

Primary Examiner—Lewis Gotts
Assistant Examiner—Cary Owens
Attorney, Agent, or Firm—Cushman, Darby & Cushman

[57] ABSTRACT

The process of the invention is directed to separating a racemic mixture of L- and D-phenyl-glycine amide, by treatments of the racemate with an optically active form of 2-pyrrolidone-5-carboxylic acid.

9 Claims, No Drawings

OPTICAL RESOLUTION OF PHENYL-GLYCINE AMIDE

BACKGROUND OF THE INVENTION

The invention relates to a process for the preparation of optically active phenyl-glycine amide by subjecting a mixture of L- and D-phenyl-glycine amide to optical resolution.

A mixture of L- and D-phenyl-glycine amide herein also denotes the racemate of phenyl-glycine amide and mixtures of the racemate with the L-isomer and/or D-isomer.

Phenyl-glycine amide can be hydrolyzed to phenyl-glycine in a simple way, e.g., by treatment with sulphuric acid, as described in Journal of the Chemical Society (1966) pages 393–397. Thus, the present process is of importance in the preparation of optically active phenyl-glycine. The prior art method for the production of optically active phenyl-glycine is a rather expensive method, in which D-phenyl-glycine is prepared by reaction of α-bromo-(D-camphor) sulphonic acid (see: Berichte 41, page 2073). This prior art method is very laborious and has the drawback that the rather expensive separating agent gets lost during the processing steps.

SUMMARY OF THE INVENTION

It has now been found that the optical resolution of phenyl-glycine amide can be effected by salt formation with optically active 2-pyrrolidone-5-carboxylic acid, wherein it is not necessary to convert the total amount of phenyl-glycine amide to a salt. Hence, the process according to the invention is characterized in that the mixture of L- and D-phenyl-glycine amide is wholly or partly converted to the salt of phenyl-glycine amide and optically active 2-pyrrolidone-5-carboxylic acid, and in that a part mainly consisting of one of the diastereoisomers of said salt is separated from the resulting product.

Phenyl-glycine amide can be prepared from the aminonitrile of phenyl-glycine in a known way by acid hydrolysis by treatment with, e.g., hydrochloric acid, or by an ammonia treatment of a phenyl-glycine alkyl ester; the phenyl-glycine alkyl ester can be obtained from both the aminonitrile and the phenyl-glycine.

One use of D-phenyl-glycine is as a starting material for the preparation of α-aminobenzyl penicillin. L-phenyl-glycine is used for preparing L-asparagine-L-phenyl-glycine alkyl ester, a sweetening agent.

DETAILED DESCRIPTION OF THE INVENTION

The invention is directed to treatment of a racemic mixture of phenyl-glycine amide with an optically active form of 2-pyrrolidone-5-carboxylic acid to produce a mixture of diastereoisomeric salts. One of the enantiomers, either D- or L-phenyl-glycine amide, may be separated from the diastereoisomeric salt mixture.

If the salt formation is effected with less than 1 mole of pyrrolidone carboxylic acid per mole of phenyl-glycine amide, use is preferably made of 0.5 mole of pyrrolidone carboxylic acid per mole of phenyl-glycine amide, so that the diastereoisomeric salt can be separated from the phenyl-glycine amide that has not been converted to salt.

The process according to the invention may be carried out in water or in a water-miscible polar organic solvent containing 1 – 4 carbon atoms in which the diastereoisomeric salts are soluble to a sufficiently different extent, such as, e.g., methanol, ethanol, isopropyl alcohol, acetone, dioxane, water or mixtures thereof. It appears that in such solvents, which need not necessarily be water-free, the salt of D-phenyl-glycine amide with D-pyrrolidone carboxylic acid (the D-D salt) is much less soluble than the salt of L-phenyl-glycine amide with D-pyrrolidone carboxylic acid (the L-D salt) and it appears that the salt of L-phenyl-glycine amide with L-pyrrolidone carboxylic acid (the L-L salt) is much less soluble than the salt of D-phenyl-glycine amide with L-pyrrolidone carboxylic acid (the D-L salt).

It is also possible to use a liquid medium in which all compounds present can be fully dissolved, to remove the solvent after solution and to subject the remaining solid substance to preferential extraction with, e.g., one solvent, e.g., water or the water-miscible polar solvents including methanol, ethanol, propanol, dioxane, water or mixtures thereof.

Treatment of the racemate of phenyl-glycine amide with the optically active 2-pyrrolidone-5-carboxylic acid is undertaken at temperatures ranging from 30° to 90° C.

The salt obtained in the process according to the invention can be separated into its components, e.g., by means of ion exchangers. By preference, a weakly basic and a strongly acid ion exchanger are used in succession, e.g., Lewatit as the weakly basic and Dowex 50 as the strongly acid ion exchanger.

After the less soluble diastereoisomeric salt has been isolated, the other isomer can be obtained from the remaining solution in various known ways.

If only one of the antipodes of the phenyl-glycine amide is desired, the undesired optically active phenyl-glycine amide may be racemized by heating in an inert solvent. Examples of solvents are water, glacial acetic acid and diethylene-glycol-dimethyl ether. The temperature in the racemization that is normally chosen is the boiling temperature of the solution at atmospheric pressure. If water is used as the solvent in the racemization, temperatures of over 150° C. will be employed, as the reaction time will become too long at lower temperatures and a long reaction time promotes hydrolysis of the amide to the acid. In that case, the use of superatmospheric pressure is necessary, of course.

The process according to the invention, which may be effected in various ways with the use of methods, which are known techniques, for the optical resolution of a mixture of optical antipodes by salt formation and subsequent racemization of the undesired component, will be further elucidated in the following examples without restricting the invention thereto.

EXAMPLE I

A solution of 9.0 g of DL-phenyl-glycine amide (0.06 gmole) in 150 ml of 100% ethanol is put in a flask provided with a stirrer, and 3.9 of D-pyrrolidone carboxylic acid (0.03 gmole) are then added to the solution at 70° C. Next, the solution is allowed to cool while being stirred, when a mass of needle-shaped crystals is formed. The crystal mass is filtered and washed on the filter with 12 ml of 100% ethanol, and then dried at 50° C. and a pressure of 12 mm Hg. Yield: 7.0 g of D-phenyl-glycine-amide-D-pyrrolidone-carboxylic acid. Yield: 83.3%. The specific rotation of this salt is $[\alpha]_D^{20} = -52°$ (C = 2; water); the term between brackets means that the specific rotation is determined in a solution of the salt in water having a concentration of 2 grams of salt in 100 milliliter of solution. According to amino-acid analysis, the salt contains 1 mole of pyrrolidone carboxylic acid per mole of phenyl-glycine amide.

3.0 g of the salt obtained is dissolved in 50 ml of distilled water and then passed over 75 ml of Lewatit ion exchanger in the amine form. Next, the ion exchanger is washed with 100 ml of distilled water. After evaporation of the resulting eluate at 30° C. and 12 mm Hg. 1.55 of crystalline product is obtained (yield 97%). This product is pure D-phenyl-glycine amide according to thin-layer chromatography. The specific rotation of this product is $[\alpha]_D^{20} = -90°$ C. (C = 1; water).

After the resulting D-phenyl-glycine amide has been converted to the hydrochloric acid salt, the specific rotation is $[\alpha]_D^{20} = -97°$ (C = 0.8; water). The specific rotation of this salt mentioned in literature is $[\alpha]_D^{20} = -100.8°$ (C = 0.8; water) (Beilstein 14, III, page 1189). It follows from a comparison of the two specific rotations that the optically active D-phenyl-glycine amide obtained according to the invention has an optical purity of 98% (98% D and 2% L).

If the hydrochloric salt of D-phenyl-glycine amide is recovered directly from the resulting D-D salt, the specific rotation of the hydrochloric acid salt is $[\alpha]_D^{20} = -100°$ (C = 0.8; water), which corresponds to an optical purity of 99.5%. From this it follows that the specific rotation is effected only very slightly in the conversion of the above-mentioned D-phenyl-glycine amide to the hydrochloric acid salt.

The direct recovery of the hydrochloric acid salt of D-phenyl-glycine amide can be effected by dissolving 1 gram of D-D salt in 5 ml of water and adding 5 ml of concentrated HCl, which will yield a crystalline precipitate of D-phenyl-glycine amide HCl. After filtration, the precipitate is washed twice with 3 ml of 100% ethanol and 10 ml of ether. After drying at 40° C. and 12 mm Hg. 0.6 g of D-phenyl-glycine amide HCl is obtained. This product is pure according to thin-layer chromatography (yield 90%).

EXAMPLE II 1.3 g (0.01 gmole) of L-pyrrolidone carboxylic acid is added to a solution of 3.0 g (0.02 gmole) of DL-phenyl-glycine amide in 50 ml of ethanol at 60° C. with stirring in the same way as in Example I. Upon cooling to room temperature, a mass of needle-shaped crystals is formed, which is filtered and washed on the filter with 10 ml of ethanol and then dried at 50° C. and 12 mm Hg. 2.2 g of L-phenyl-glycine-amide-L-pyrrolidone-carboxylic acid are obtained (yield 80%).

This salt is converted to L-phenyl-glycine amide.HCL, as described in Example I. The specific rotation of the resulting hydrochloric acid salt is $[\alpha]_D^{20} = +102.6°$ (C = 0.8; water).

EXAMPLE III 2.6 g (0.02 gmole) of D-pyrrolidone carboxylic acid is added to a solution 6.0 g (0.04 gmole) of DL-phenyl-glycine amide in 100 ml of isopropanol in a flask at 70° C. with stirring. Next, another 30 ml of isopropanol are added and the reaction mixture is allowed to cool to room temperature while being stirred. The resulting crystal mass is filtered, washed on the filter with twice 20 ml of isopropanol, and then dried at 50° C. and 12 mm Hg. The weight of the dried crystals is 5.2 grams (yield 92%).

The specific rotation of the D-phenyl-glycine amide.HCl obtained from the D-D salt as described in Example I is $[\alpha]_D^{20} = -100°$ (C = 0.8; water). In literature (Beilstein 14, III page 1189) a specific rotation of D-phenyl-glycine amide.HCl is mentioned of: $[\alpha]_D^{20} = -100.8°$ (C = 0.8; water).

The mother liquor obtained in the above filtration is evaporated at 40° C. and 12 mm Hg. when 3.3 g of evaporation residue remains.

0.5 g of this evaporation residue is dissolved in 5 ml of water, after which 5 ml of concentrated hyrochloric acid is added. Upon filtration and washing with twice 3 ml of ethanol and 10 ml of ether, 0.6 g of phenyl-glycine amide.HCl is obtained, which is pure according to thin-layer chromatography. The specific rotation of this phenyl-glycine amide. HCl is $[\alpha]_D^{20} = +78°$ (C = 0.8; water).

From this it follows that the evaporation residue mainly consists of L-phenyl-glycine amide.

2.8 g of the evaporation residue are converted to L-phenyl-glycine amide by means of Lewatit ion exchanger in the way described in Example I.

0.5 g of this L-phenyl-glycine amide is dissolved in 15 ml of water and the resulting solution is heated at 160° -170° C. for 45 minutes in a small autoclave by means of an oil bath. Under these conditions the L-phenyl-glycine amide racemizes almost completely. After the solution has been cooled and diluted with water to C = 0.8, the specific rotation is determined: $[\alpha]_D^{20} = +1.1$ (C = 0.8; water).

Amino-acid analysis of the racemized product gave the following results: 92.5% of phenyl-glycine amide and 7.5% of phenyl-glycine.

EXAMPLE IV

A mixture of 3.0 g (0.02 gmole) of DL-phenyl-glycine amide and 2.6 g (0.02 gmole) of L-pyrrolidone carboxylic acid is dissolved in 10 ml of water in a flask at 100° C. Upon cooling, the resulting crystals are filtered and washed on the filter with 5 ml of methanol. After drying of the filtrate at 50° C. and 12 mm Hg. 1.5 g of L-phenyl-glycine amide crystals are obtained (yield 53%).

The specific rotation of the L-phenyl-glycine amide.HCl obtained from the crystal mass is $[\alpha]_D^{20} = +101.9°$ (C = 0.8; water).

EXAMPLE V

Example III is repeated, but the racemization is effected in glacial acetic acid.

0.5 of L-phenyl-glycine amide is added to 50 ml of glacial acetic acid in a flask provided with a reflux cooler, after which the solution is heated to the boiling point (120° C.). This temperature is maintained for 35 minutes.

The specific rotation of the original L-phenyl-glycine amide is $[\alpha]_D^{20} = +175°$ (C = 1; glacial acetic acid).

After the phenyl-glycine amide has cooled, the specific rotation is determined, which amounts to $[\alpha]_D^{20} = +12.5$ (C = 1; glacial acetic acid).

From this it follows that the L-phenyl-glycine amide has been racemized almost completely.

EXAMPLE VI

A solution of 0.3 g of L-phenyl-glycine amide obtained according to the process described in Example III in 18 ml of diethylene-glycol dimethyl ether is boiled at 162° C. for 1 hour.

The specific rotation of the L-phenyl-glycine amide before the racemization is $[\alpha]_D^{20} = +90°$ (C = 1.66; diethylene-glycol dimethyl ether).

The specific rotation of the phenyl-glycine amide after cooling is $[\alpha]_D^{20} = +0.5°$ (C = 1.66; diethylene-glycol dimethyl ether).

0.3 g of DL-phenyl-glycine amide is obtained upon evaporation at 50° C. and 1 mm Hg. (yield 100%).

EXAMPLE VII

A solution of 3.0 g (0.02 gmole) of DL-phenyl-glycine amide in 45 ml of acetone and 5 ml of water is transferred to a flask provided with a stirrer and, subsequently, 1.3 g (0.01 gmole) of D-pyrrolidone carboxylic acid is added to the solution. While stirring the solution is heated to 50° C. and stirring is continued for 15 minutes at said temperature.

After the solution has cooled, stirring is continued for 30 more minutes during whch a crystal mass forms. The mass is filtered and washed with twice 10 ml of acetone and is then dried at 50° C. and 12 mm Hg. Yield: 2.7 g of D-phenyl-glycine-amide-D-pyrrolidone-carboxylic acid at an effficiency of 96.4%.

The D-phenyl-glycine-amide-D-pyrrolidone-carboxylic acid salt obtained is converted to D-phenyl-glycine-amide.HCl in the way described in Example I, the specific rotation being: $[\alpha]_D^{20} = -101.2°$ (C = 0.8; water).

EXAMPLE VIII

A mixture of 4.5 g (0.03 gmole) of DL-phenyl-glycine amide, 2.0 g (0.015 gmole) of L-pyrrolidone carboxylic acid, 22 ml of acetone and 3 ml of water is stirred in a flask for half an hour at 50° C. Next, stirring is continued for 3 more hours at room temperature.

The resulting L-phenyl-glycine-amide-L-pyrrolidone-carboxylic acid salt is filtered and washed with 10 ml of acetone and subsequently dried. Yield: 4.5 g.

The filtrate is acidulated with 2 ml of HCl and the D-phenyl-glycine-amide.HC1 obtained is filtered. After having been washed with 3 times 15 ml of acetone, the crystal mass is dried. D-phenyl-glycine amide yield: 2.4 g. Efficiency: 86%. Specific rotation $[\alpha]_D^{25} = -84°$ (C = 0.8; H$_2$O).

What is claimed is:

1. A process for isolating an optically active form of phenyl-glycine amide, from racemic mixtures of the enantiomers of phenyl-glycine amide, comprising providing a racemic mixture of D- and L-phenyl-glycine amide and an optically active form of 2-pyrrolidone-5-carboxylic acid; treating said racemic mixture with the 2-pyrrolidone-5-carboxylic acid to form the corresponding salts of said optically active 2-pyrrolidone-5-carboxylic acid and said enantiomers; and separating from the mixture an optically active form of phenyl-glycine amide in the form of a salt of said 2-pyrrolidone-5-carboxylic acid.

2. Process according to claim 1, characterized in that the salt formation is effected in a liquid medium which is water; a water-miscible polar organic solvent containing 1 – 4 carbon atoms; or a mixture thereof, in which the diastereoisomeric salts are soluble to a different extent.

3. Process according to claim 2, characterized in that the liquid medium used is methanol, ethanol, isopropyl alcohol, acetone, dioxane, water, or a mixture thereof.

4. Process according to claim 2, wherein said step of treating is undertaken at a temperature ranging from 30° to 90° C.

5. Process according to claim 1, characterized in that 1 mole of 2-pyrrolidone-5-carboxylic acid is used per mole of DL-phenyl-glycine amide.

6. Process according to claim 1, characterized in that 0.5 mole of 2-pyrrolidone-5-carboxylic acid is used per mole of DL-phenyl-glycine amide.

7. Process according to claim 1, wherein the enantiomer which is not separated as a salt of the optically active 2-pyrrolidone-5-carboxylic acid is subsequently racemized by heating in a solvent.

8. Process according to claim 1, wherein 2-pyrrolidone-5-carboxylic acid is in the L-form.

9. D- and L-2-pyrrolidone-5-carboxylic salts of optically active phenyl-glycine amide.

* * * * *